(12) United States Patent
Jeong et al.

(10) Patent No.: US 12,324,650 B2
(45) Date of Patent: *Jun. 10, 2025

(54) INTRAORAL SCANNER HAVING TOMOGRAPHIC IMAGING FUNCTION AND METHOD FOR DETECTING CRACKS IN ORAL STRUCTURES USING THE SAME

(71) Applicants: Huvitz Co., Ltd., Anyang-si (KR); Ossvis Co., Ltd., Anyang-si (KR); Kyungpook Nat'l Univ Industry-Academic Coop Fndn, Daegu (KR)

(72) Inventors: Hyo Sang Jeong, Anyang-si (KR); Su Min Han, Anyang-si (KR); Jee Hyun Kim, Daegu (KR); Kyu Bok Lee, Daegu (KR); Keun Ba Da Son, Daegu (KR); Weon Joon Lee, Anyang-si (KR)

(73) Assignees: Huvitz Co., Ltd., Anyang-si (KR); Ossvis Co., Ltd., Anyang-si (KR); Kyungpook National University Industry-Academic Cooperation Foundation, Daegu (KR)

(*) Notice: Subject to any disclaimer, the term of this patent is extended or adjusted under 35 U.S.C. 154(b) by 241 days.

This patent is subject to a terminal disclaimer.

(21) Appl. No.: 18/171,987

(22) Filed: Feb. 21, 2023

(65) Prior Publication Data
US 2023/0263396 A1    Aug. 24, 2023

(30) Foreign Application Priority Data
Feb. 21, 2022    (KR) .................. 10-2022-0022433

(51) Int. Cl.
*A61B 5/00*    (2006.01)
(52) U.S. Cl.
CPC .......... *A61B 5/0088* (2013.01); *A61B 5/0066* (2013.01)

(58) Field of Classification Search
CPC ................ A61B 5/0088; A61B 5/0066; A61B 2090/3735; A61B 5/0073; A61B 5/682
See application file for complete search history.

(56) References Cited

U.S. PATENT DOCUMENTS 10,517,482 B2    12/2019    Sato et al.
2009/0079993 A1*    3/2009    Yatagai ................ A61B 5/7257
                                                                    356/497

(Continued)

FOREIGN PATENT DOCUMENTS

| KR | 10-2088951 B1 | 4/2020 |
| KR | 10-2022-0085364 A | 6/2022 |
| KR | 10-2023-0084032 A | 6/2023 |

OTHER PUBLICATIONS

Korean Office Action for counterpart Korean Patent Application No. 10-2022-0022433, dated Jan. 19, 2024.

(Continued)

*Primary Examiner* — Gerald Johnson
(74) *Attorney, Agent, or Firm* — United One Law Group LLC; Kongsik Kim; Jhongwoo Peck

(57) ABSTRACT

An intraoral scanner having a tomographic imaging function includes an OCT body configured to obtain an internal cross-sectional image of an oral structure; an OCT scan probe configured to irradiate the layer measurement light emitted from the OCT body onto the oral structure and transfer the reflected light to the OCT body; and a control/processing unit configured to control the OCT body, take a tomographic image of the oral structure, obtain two or more two-dimensional cross-sectional images, extract an internal crack area for the respective two-dimensional cross-sectional images, calculate cross-sectional position information of the internal crack, then arrange the position information of the internal crack obtained from the respective two-dimensional cross-sectional images in positions where the (Continued)

respective two-dimensional cross-sectional images have been obtained, and obtain three-dimensional shape information of the internal crack.

6 Claims, 5 Drawing Sheets

(56) References Cited

U.S. PATENT DOCUMENTS

2019/0029522 A1   1/2019   Sato et al.
2019/0117078 A1   4/2019   Sharma et al.

OTHER PUBLICATIONS

European search report for counterpart EP application No. 23156482. 4, dated Jul. 6, 2023.
Tabata et al., "Assessment of enamel cracks at adhesive cavosurface margin using three dimensional swept-source optical coherence tomography," Journal of Dentistry, vol. 61, 28-32, Apr. 19, 2017, Elsevier.
Abstract of Segarra et al., "Three-Dimensional Analysis of Enamel Crack Behavior Using Optical Coherence Tomography," Journal of Dental Research, 96(3), 308-14, Mar. 2017.
Li et al., "Detection and analysis of enamel cracks by ICG-NIR fluorescence dental imaging," Ann. N.Y. Acad. Sci.,, 1475, 52-63, Jun. 9, 2020.
Abstract of Kim et al., "Automatic detection of tooth cracks in optical coherence tomography images," Journal of periodontal & implant science, 47(1), 41-50, Feb. 2017.

\* cited by examiner

A  B

INTRAORAL SCANNER HAVING TOMOGRAPHIC IMAGING FUNCTION AND METHOD FOR DETECTING CRACKS IN ORAL STRUCTURES USING THE SAME

CROSS-REFERENCE TO RELATED APPLICATION

This application claims priority to Korean Patent Application No. 10-2022-0022433 filed on Feb. 21, 2022, which is incorporated herein by reference in its entirety.

STATEMENT REGARDING SPONSORED RESEARCH

Following are results of a study on the "Leaders in Industry-university Cooperation 3.0" Project, supported by the Ministry of Education and National Research Foundation of Korea.

TECHNICAL FIELD

The present disclosure relates to an intraoral scanner having a tomographic imaging function, and more particularly, to an intraoral scanner having a tomographic imaging function capable of inspecting the state of cracks in oral structures such as teeth and dental filling materials, and a method for detecting cracks in oral structures using the same.

RELATED ART

Generally, in dental hospitals or the like, the shape and structure of teeth or tissues inside a patient's oral cavity are examined, based on which the oral condition of the patient is diagnosed, followed by making prostheses or treating dental diseases. In order to examine oral structures such as teeth, tissues, or the like in the oral cavity, optical intraoral scanners that irradiate the measurement light to the oral structure, detect reflected light generated by being reflected from the oral structure with an image sensor, and obtain surface shape information of the oral structure are commonly used. However, in the case of such an intraoral scanner, the surface shape information of the oral structure can be obtained, but the internal state of the oral structure cannot be examined. On the other hand, although such methods as X-ray imaging and computed tomography (CT) that obtain two-dimensional or three-dimensional shapes of oral structures by irradiating radiation from the outside of the oral cavity to the inside of the oral cavity are also commonly used, there is a disadvantage in that it is difficult to obtain high-resolution three-dimensional shapes and internal structural information of oral structures with these methods. If there occur cracks in teeth or dental filling materials, these cracks can cause dental caries or damages around the tooth and the filling material, but there is a disadvantage in that it is difficult to detect such cracks early with conventional methods.

Recently, a method of obtaining external shape and internal layer images of an oral structure by using a combined device with an optical scanner and an optical coherence tomography (OCT) device incorporated therein has been attempted (Refer to Korean Patent Application Nos. 10-2020-0175365 and 10-2021-0171392). Optical coherence tomography (OCT) is a device that obtains the surface shape and internal layer images of an object to be inspected by transmitting measurement light having a wavelength in the near-infrared region through the object to be inspected and detecting the reflected light reflected from the surface and each layer on the inside of the object to be inspected by utilizing the coherence property of light. Using optical coherence tomography (OCT) allows surface and internal layer images of an object to be inspected to be obtained non-invasively at a high resolution of the level of the wavelength of the measurement light irradiated to the object to be inspected, e.g., in the order of several μm.

PRIOR ART LITERATURE

1. Korean Patent Registration No. 10-2088951
2. Korean Patent Application No. 10-2020-0175365
3. Korean Patent Application No. 10-2021-0171392

SUMMARY

It is an object of the present disclosure to provide an intraoral scanner having a tomographic imaging function capable of inspecting the state of cracks in oral structures such as teeth and dental filling materials, and a method for detecting cracks in oral structures.

It is another object of the present disclosure to provide an intraoral scanner having a tomographic imaging function capable of obtaining information such as the depth, width, and range of cracks occurred in oral structures by scanning the oral structures in three dimensions and of inspecting the state of tooth cracks using this, and a method for detecting cracks in the oral structures.

In order to achieve the above objects, the present disclosure provides an intraoral scanner having a tomographic imaging function, comprising: an OCT body 6 configured to obtain an internal cross-sectional image of an oral structure T by transmitting layer measurement light through the oral structure T and detecting reflected light reflected by a surface and an inside of the oral structure T; an OCT scan probe 8 configured to irradiate the layer measurement light emitted from the OCT body 6 onto the oral structure T and transfer the reflected light reflected from the oral structure T to the OCT body 6; and a control/processing unit 48 configured to control the OCT body 6, take a tomographic image of the oral structure T while proceeding in a predetermined direction along the surface of the oral structure T, obtain two or more two-dimensional cross-sectional images of the oral structure T, extract an internal crack area for the respective two-dimensional cross-sectional images obtained, calculate cross-sectional position information of the internal crack, then arrange the position information of the internal crack obtained from the respective two-dimensional cross-sectional images in positions where the respective two-dimensional cross-sectional images have been obtained, and obtain three-dimensional shape information of the internal crack.

In addition, the present disclosure provides a method for detecting cracks in an oral structure using an intraoral scanner having a tomographic imaging function, comprising: obtaining two or more two-dimensional cross-sectional images 60a, 60b, 60c, and 60d of an oral structure T by taking a tomographic image of the oral structure T while proceeding in a predetermined direction along a surface of the oral structure T; calculating cross-sectional position information of an internal crack by extracting each internal crack region for the respective two-dimensional cross-sectional images 60a, 60b, 60c, and 60d obtained; and obtaining three-dimensional shape information of the internal crack by arranging the position information of the internal crack obtained from the respective two-dimensional cross-sectional images 60a, 60b, 60c, and 60d in positions y1, y2, y3, and y4 at which the respective two-dimensional cross-sectional images 60a, 60b, 60c, and 60d have been obtained.

According to the intraoral scanner having a tomographic imaging function and the method for detecting cracks in the oral structures in accordance with the present disclosure, it is possible to obtain information such as the depth, width, and range of cracks occurred in the oral structures by scanning the oral structures in three dimensions and to inspect the state of tooth cracks using this.

DETAILED DESCRIPTION

Hereinafter, the present disclosure will be described in detail with reference to the accompanying drawings.

Figure 1:
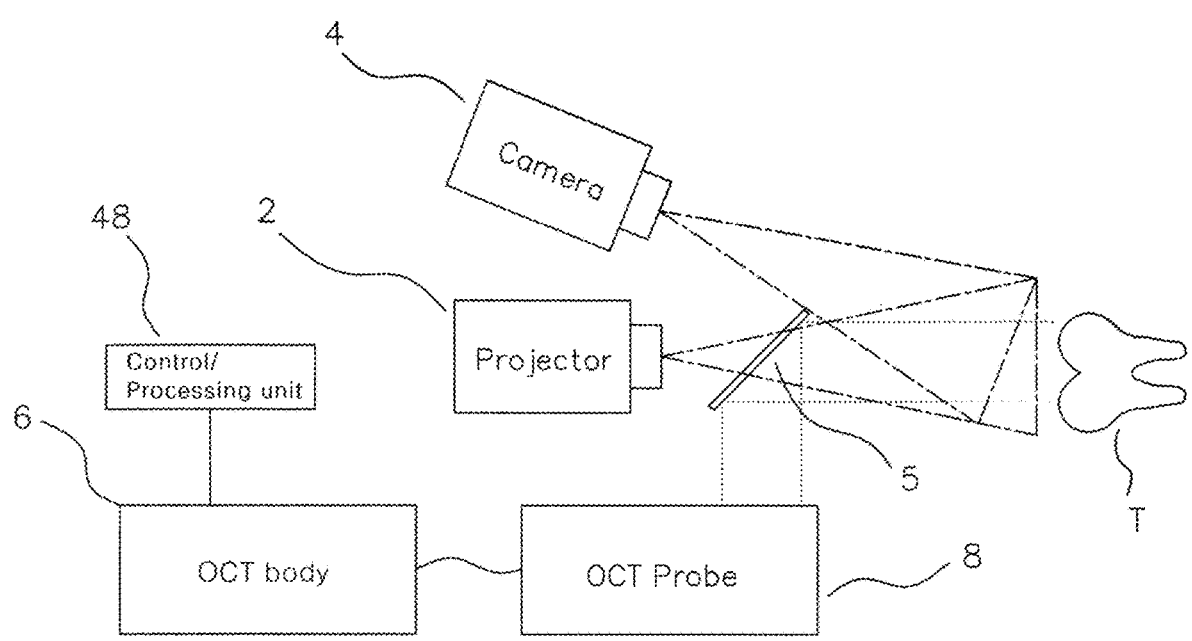
FIG. 1 is a diagram showing the configuration of an intraoral scanner having a tomographic imaging function in accordance with one embodiment of the present disclosure.

FIG. 1 is a diagram showing the configuration of an intraoral scanner having a tomographic imaging function in accordance with one embodiment of the present disclosure. As shown in FIG. 1, an intraoral scanner having a tomographic imaging function in accordance with the present disclosure may include an optical coherence tomography (OCT) body 6, an OCT scan probe 8, and a control/processing unit 48, and may further include a shape measurement light projector 2, a shape measurement camera 14, and a beam splitter 5 as desired.

The OCT body 6 is a device that obtains internal cross-sectional images of an oral structure T by transmitting layer measurement light (e.g., near-infrared light) through the oral structure T and detecting reflected light (scattered light) reflected by the surface and the inside, specifically, each layer, of the oral structure T, and obtains layer information inside an object by using the coherence properties of the layer measurement light. The layer measurement light may be broadband low-coherence light having a short coherence distance, and may be, for example, near-infrared light, specifically, near-infrared light having a wavelength of 750 to 1500 nm. The OCT scan probe 8 is a device that irradiates the layer measurement light emitted from the OCT body 6 to a desired position on the oral structure T, and transfers the reflected light reflected by the oral structure T to the OCT body 6.

The control/processing unit 48 controls the OCT main body 6 and detects cracks occurred in the oral structure T from the internal cross-sectional images of the oral structure T obtained by the OCT main body 6. Specifically, the control/processing unit 48 controls the OCT body 6, takes tomographic images of the oral structure T while proceeding in a predetermined direction along the surface of the oral structure T, obtains two or more two-dimensional cross-sectional images of the oral structure T, extracts internal crack areas for the respective two-dimensional cross-sectional images obtained, calculates the cross-sectional position information of the internal cracks, then arranges the position information of the internal cracks obtained from the respective two-dimensional cross-sectional images in the positions where the respective two-dimensional cross-sectional images have been obtained, and obtains three-dimensional shape information of the internal cracks.

The shape measurement light projector 2 irradiates shape measurement light for obtaining a shape image of the oral structure T such as teeth. As the shape measurement light, any measurement light that can obtain a shape image of the oral structure T may be used without limitation, and preferably visible light, e.g., visible light having a wavelength of 400 to 700 nm may be used. The shape measurement camera 4 is a device that obtains a surface shape image of the oral structure T by detecting reflected light formed by the shape measurement light being reflected by the surface of the oral structure T, and includes a conventional image sensor. In operation, the shape measurement light is outputted from the shape measurement light projector 2, the outputted shape measurement light passes through the beam splitter 5 and then irradiates the oral structure T, and the reflected light reflected by the oral structure T is detected by the shape measurement camera 4, thereby obtaining a surface shape image of the oral structure T. At this time, the two-dimensional image of the oral structure T obtained by the shape measurement camera 4 may be converted into a three-dimensional image using a triangulation method or the like.

The beam splitter 5 is a device that separates the optical paths of the shape measurement light emitted from the shape measurement light projector 2 and of the layer measurement light emitted from the OCT scan probe 8, and separates a shape acquisition optical system formed by the shape measurement light projector 2 and the shape measurement camera 4 from a layer acquisition optical system formed by the OCT body 6 and the OCT scan probe 8. For example, as shown in FIG. 1, the beam splitter 5 may be a dichroic mirror that transmits the shape measurement light emitted from the shape measurement light projector 2 and reflects the layer measurement light emitted from the OCT scan probe 6, thereby irradiating the oral structure T with the shape measurement light and the layer measurement light, and separates and transfers each reflected light to the shape acquisition optical system, specifically the shape measurement camera 4 and the layer acquisition optical system, specifically the OCT body 6.

Figure 2:
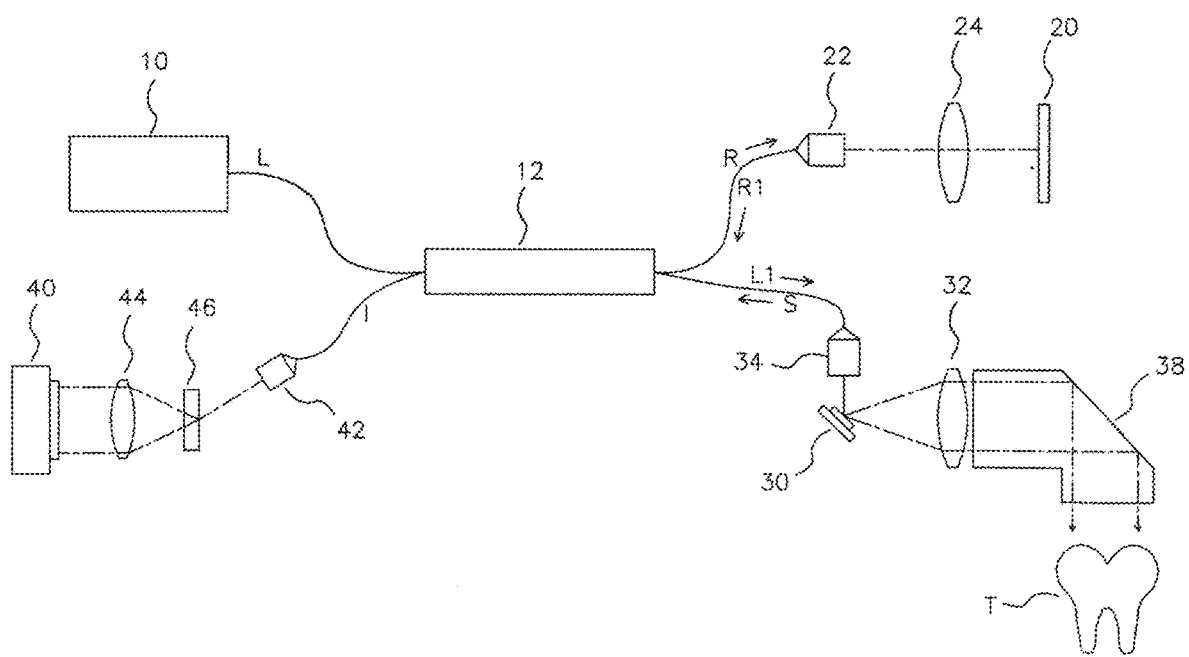
FIG. 2 is a diagram showing the configuration of an optical coherence tomography device that can be applied to the intraoral scanner of the present disclosure.

FIG. 2 is a diagram showing the configuration of an optical coherence tomography device (OCT) that can be applied to the intraoral scanner of the present disclosure. As shown in FIG. 2, an optical coherence tomography (OCT) device that can be applied to the present disclosure includes a light source 10, a beam splitter 12, a reference mirror 20, a scan unit 30, and a photodetector 40. Here, the light source 10, the beam splitter 12, the reference mirror 20, and the photodetector 40 may form the OCT body 6 of FIG. 1, and the scan unit 30 may be mounted on the OCT scan probe 8 of FIG. 1.

The light source 10 generates the layer measurement light L that is irradiated onto the oral structure T. The beam splitter 12 splits the layer measurement light L into a reference light R and a sample measurement light L1, and irradiates the reference light R onto the reference mirror 20 and the sample measurement light L1 onto the oral structure T. The beam splitter 12 may split the measurement light L into, for example, a reference light R and a sample measurement light L1 with an intensity of 50:50. The beam splitter 12 is also referred to as an optical coupler since it serves to superimpose a reference reflected light R1 and a signal reflected light S as well, which will be described later. The scan unit 30 reflects the sample measurement light L1 and guides the sample measurement light L1 to the oral structure T through an objective lens 32. As the scan unit 30, a micro-electro-mechanical system (MEMS) mirror capable of sequentially scanning the imaging positions on the oral structure T by adjusting the reflection angle of the sample measurement light L1 may be used. For example, the MEMS mirror rotates based on two axes (e.g., x-axis and y-axis in an orthogonal relationship, see FIG. 3) and is made to scan sequentially the plane (x-y plane) on which the oral structure T is located. The sample measurement light L1 is irradiated into the oral structure T in a direction perpendicular to the plane (z-axis direction, orthogonal to the x-axis and y-axis, see FIG. 3), thereby obtaining a three-dimensional layer image of the oral structure T.

When the sample measurement light L1 is irradiated onto the oral structure T, the sample measurement light L1 is reflected and scattered on the surface and inside of the oral structure T, thereby generating the signal reflected light S. On the other hand, the reference light R is reflected by the reference mirror 20, thereby generating the reference reflected light R1. The signal reflected light S generated is guided to the scan unit 30 through the objective lens 32, and the scan unit 30 guides the signal reflected light S to the beam splitter 12. The signal reflected light S and the reference reflected light R1 are superimposed at the beam splitter 12, thereby generating interference light I. The photodetector 40 detects the interference light I and thus obtains surface and internal image signals of the oral structure T. The optical coherence tomography device used in the present disclosure may include optical elements such as collimators 22, 34, and 42, lenses 24, 32, and 44, grating 46, and a probe tip 38 that transfers the measurement light L1 to a desired imaging position on the oral structure T and transfers the reflected light S reflected by the oral structure T to the scan unit 30, in order to focus, reflect, transfer, or detect various lights such as the sample measurement light L1, the reference light R, and the interference light I as desired. In this way, using the probe 38 made smaller as the MEMS scanner 30 makes it possible to readily scan teeth in the oral cavity in three dimensions.

Figure 3:
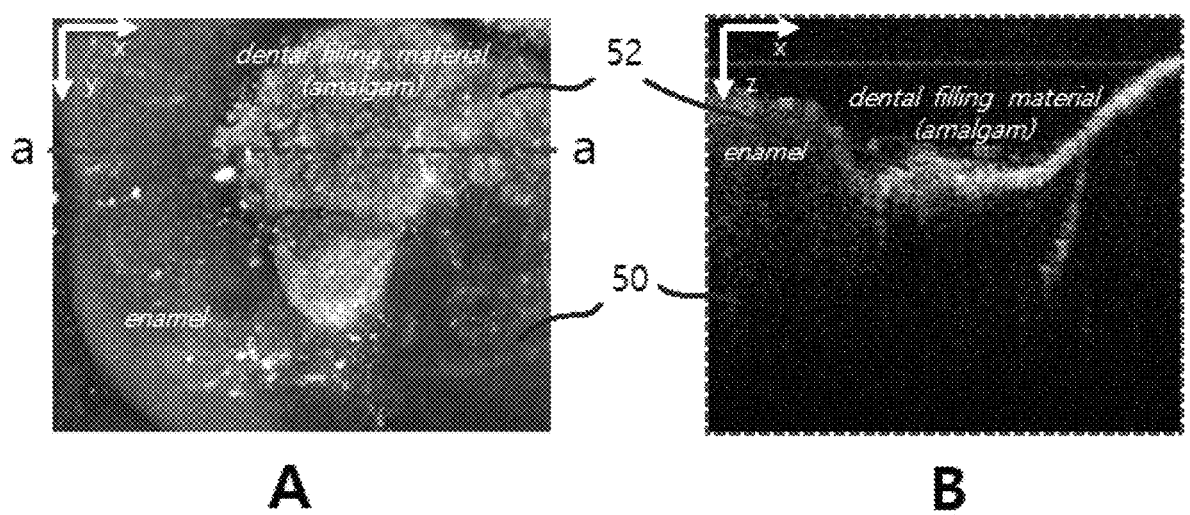
FIG. 3 shows surface (A) and cross-sectional (B) photographs of a tooth obtained using an intraoral scanner having a tomographic imaging function in accordance with the present disclosure.

FIG. 3 shows surface (A) and cross-sectional (B) photographs of a tooth obtained using an intraoral scanner having a tomographic imaging function in accordance with the present disclosure. As shown in A of FIG. 3, using the intraoral scanner having a tomographic imaging function in accordance with the present disclosure allows the entire plane on which the tooth 50 is located (x-y plane) to be scanned while proceeding in a certain direction, for example, in the y direction in the plane on which the oral structure T, i.e., the tooth 50 is located (x-y plane). In addition, by using the tomographic imaging function, a cross-sectional image (x-z plane image, a-a cross-sectional image of A in FIG. 3) of the tooth 50 can be obtained at each y position, as shown in B of FIG. 3. It can be confirmed from A of FIG. 3 that the central portion of the surface of the tooth 50 is filled with amalgam as the filling material 52, and from B of FIG. 3 that a crack has occurred in the filling material 52. On the other hand, if the filling material 52 is a resin that transmits the measurement light, the width and depth to which the filling material 52 is filled may also be checked.

Figure 4:
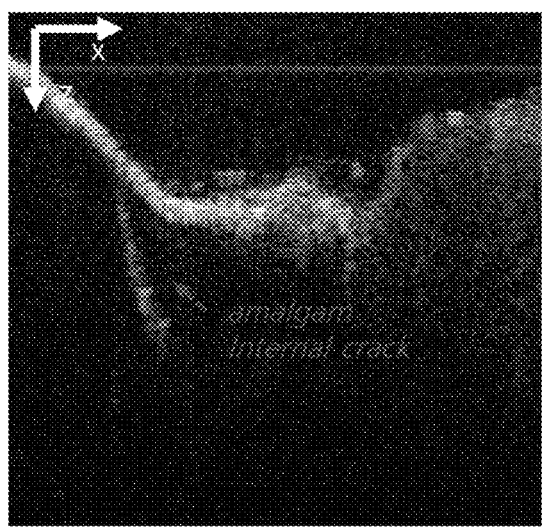
FIG. 4 is one example of a cross-sectional image of a tooth obtained using an intraoral scanner having a tomographic imaging function in accordance with the present disclosure.
Figure 4:
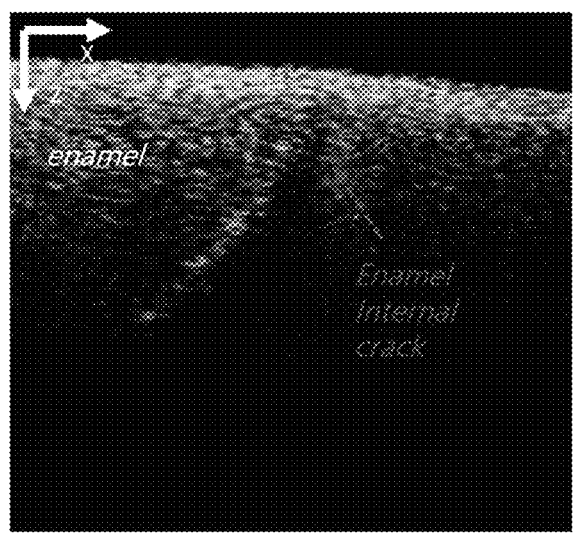

FIG. 4 is one example of a cross-sectional image of a tooth obtained using an intraoral scanner having a tomographic imaging function in accordance with the present disclosure, and shows photographs of a cross-sectional image of a tooth in which an internal crack has occurred in the amalgam that is the dental filling material 52 (A of FIG. 4, an x-z plane image), and a cross-sectional image of a tooth in which an internal crack has occurred in the enamel of the tooth 50 (B of FIG. 4, an x-z plane image). Therefore, it is possible to determine the cross-sectional state of the crack in the oral structure T from the cross-sectional image of the oral structure T obtained using the intraoral scanner having a tomographic imaging function in accordance with the present disclosure. In other words, according to the present disclosure, it is possible to check cracks inside teeth or the degree of cracks (depth, range, internal volume, etc.) inside dental filling materials (amalgam, resin, etc.), which are difficult to visually check, from the cross-sectional images of the oral structure T.

Figure 5:
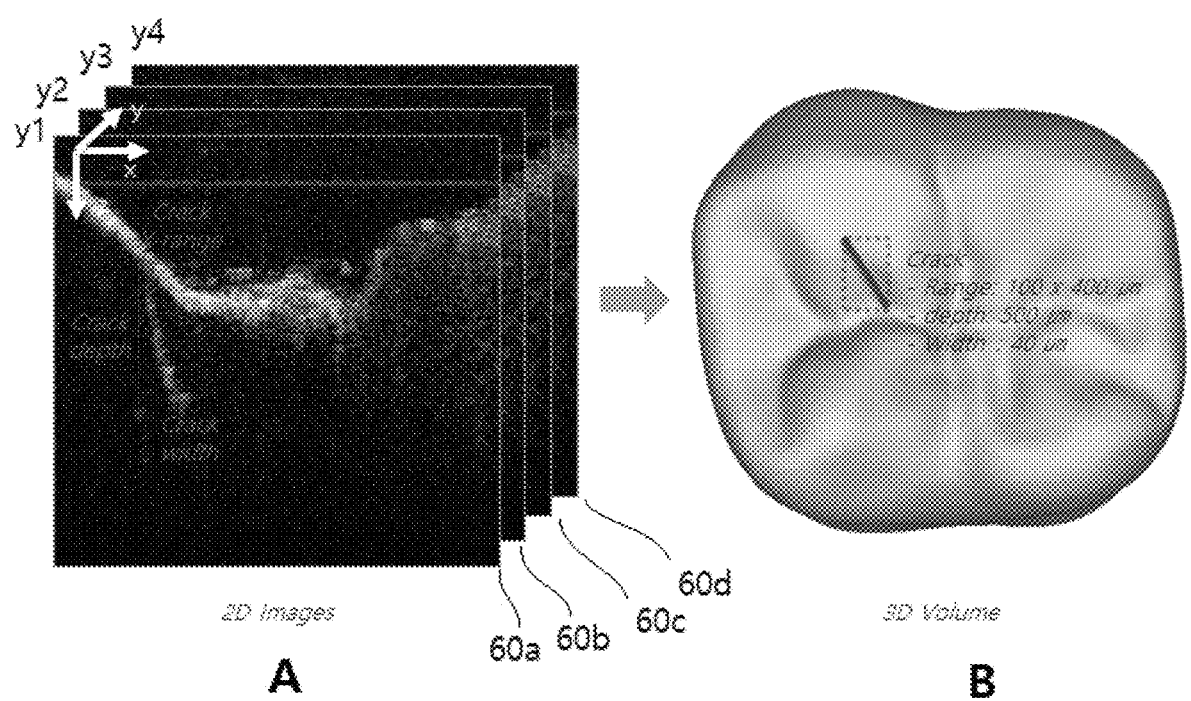
FIG. 5 is a view for describing a method for detecting cracks in an oral structure by using an intraoral scanner having a tomographic imaging function in accordance with the present disclosure.

Next, a method for detecting cracks in an oral structure in accordance with the present disclosure will be described with reference to FIG. 5. In order to detect cracks in an oral structure according to the present disclosure, first, a tomographic image of the oral structure T is taken while proceeding in a predetermined direction (e.g., y direction, y1, y2, y3, and y4 in FIG. 5) along the surface of the oral structure T (e.g., teeth), as shown in A of FIG. 5, thereby obtaining two or more two-dimensional cross-sectional images 60a, 60b, 60c, and 60d (x-z plane images) of the oral structure T. Here, if the number of two-dimensional cross-sectional images 60a, 60b, 60c, and 60d obtained is too small, the position information of internal cracks decreases and thus the accuracy of the three-dimensional shape information of the internal cracks drops, and the greater the number of two-dimensional cross-sectional images 60a, 60b, 60c, and 60d obtained, the better the accuracy of the three-dimensional shape information of the internal cracks, but there is a drawback in that the computational burden for obtaining the three-dimensional shape information of the internal cracks increases. Therefore, the number of two-dimensional cross-sectional images 60a, 60b, 60c, and 60d obtained can be appropriately set to reduce the computational burden while ensuring the accuracy of the required three-dimensional shape information, and may be, for example, four or more, preferably 5 to 200, more preferably 10 to 150, and still more preferably 15 to 100. If the three-dimensional shape information is extracted by processing the two-dimensional cross-sectional images in this way, two-dimensional image processing can be carried out in real-time while obtaining two-dimensional cross-sectional images, and accordingly, there is an advantage of being able to provide the three-dimensional shape information quickly when three-dimensional scanning is completed.

Next, each internal crack region is extracted for the respective two-dimensional cross-sectional images 60a, 60b, 60c, and 60d obtained, thereby calculating the cross-sectional position information of the internal crack, e.g., information such as the depth, x-range, and width of the internal crack. The position information of the internal crack obtained as such corresponds to the position information on the cross-section of the internal crack, i.e., on the x-z plane, obtained at each cross-sectional position of the oral structure T, i.e., at each y position y1, y2, y3, and y4. Next, the position information of the internal crack obtained from the respective two-dimensional cross-sectional images 60a, 60b, 60c, and 60d is arranged in the respective y positions y1, y2, y3, and y4, thereby obtaining three-dimensional shape information (3D volume data) of the internal crack, as shown in B of FIG. 5. In this way, when the three-dimensional shape information (3D volume data) of the internal crack is obtained, the maximum depth, width, range (formed position), and the like of the internal cracks can be known, and thus, it is possible to detect and evaluate internal cracks formed in oral structures such as teeth and dental filling materials.

In the present disclosure, the oral structures T include teeth and dental filling materials, but are not limited thereto. Although the present disclosure has been described with reference to the accompanying drawings and illustrative embodiments in the above, the present disclosure is not limited to what is shown in the drawings and the embodiments described above. In the following claims, reference numerals are indicated to aid understanding, but the scope of the following claims should not be limited to what is shown by the reference numerals and in the drawings and should be construed to encompass all modifications, and equivalent constructions and functions of the illustrative embodiments.

The invention claimed is:

1. An intraoral scanner having a tomographic imaging function, comprising:
    an OCT body configured to obtain an internal cross-sectional image of an oral structure by transmitting layer measurement light through the oral structure and detecting reflected light reflected by a surface and an inside of the oral structure;
    an OCT scan probe configured to irradiate the layer measurement light emitted from the OCT body onto the oral structure and transfer the reflected light reflected from the oral structure to the OCT body; and
    a control/processing unit configured to control the OCT body, take a tomographic image of the oral structure while the layer measurement light proceeding in a predetermined direction along the surface of the oral structure, obtain two or more two-dimensional cross-sectional images of the oral structure, extract an internal crack area for the respective two-dimensional cross-sectional images obtained, calculate cross-sectional position information of the internal crack, then arrange the position information of the internal crack obtained from the respective two-dimensional cross-sectional images in each position where the respective two-dimensional cross-sectional images have been obtained, and thereby obtain three-dimensional shape information of the internal crack.

2. The intraoral scanner having a tomographic imaging function of claim 1, further comprising:
    a shape measurement light projector configured to irradiate shape measurement light for obtaining a shape image of the oral structure; and
    a shape measurement camera configured to obtain a surface shape image of the oral structure by detecting reflected light formed by the shape measurement light being reflected by the surface of the oral structure.

3. The intraoral scanner having a tomographic imaging function of claim 2, further comprising:
    a beam splitter configured to separate optical paths of the shape measurement light emitted from the shape measurement light projector and of the layer measurement light emitted from the OCT scan probe.

4. The intraoral scanner having a tomographic imaging function of claim 1, wherein the oral structure is a tooth or a dental filling material.

5. A method for detecting cracks in an oral structure using an intraoral scanner having a tomographic imaging function, comprising:
    obtaining two or more two-dimensional cross-sectional images of an oral structure by taking a tomographic image of the oral structure while layer measurement light proceeding in a predetermined direction along a surface of the oral structure;
    extracting each internal crack region for the respective two-dimensional cross-sectional images obtained and calculating cross-sectional position information of the internal crack; and
    arranging the position information of the internal crack obtained from the respective two-dimensional cross-sectional images in each position at which the respective two-dimensional cross-sectional images have been obtained, and thereby obtaining three-dimensional shape information of the internal crack.

6. The method for detecting cracks in an oral structure of claim 5, wherein the number of the two-dimensional cross-sectional images of the oral structure for which the cross-sectional position information of the internal crack is calculated is 5 to 200.

* * * * *